United States Patent
Kangas et al.

(10) Patent No.: US 11,981,628 B2
(45) Date of Patent: *May 14, 2024

(54) USE OF A METHOD FOR REDUCTION OF HEAVY END FORMATION AND CATALYST LOSS IN A HYDROFORMYLATION PROCESS COMPRISING A BIDENTATE PHOSPHITE LIGAND

(71) Applicant: PERSTORP AB, Perstorp (SE)

(72) Inventors: Matias Kangas, Helsingborg (SE); Stefan Nilsson, Munka-Ljungby (SE)

(73) Assignee: PERSTORP AB, Perstorp (SE)

( * ) Notice: Subject to any disclaimer, the term of this patent is extended or adjusted under 35 U.S.C. 154(b) by 219 days.

This patent is subject to a terminal disclaimer.

(21) Appl. No.: 17/625,892

(22) PCT Filed: Jun. 12, 2020

(86) PCT No.: PCT/SE2020/050612
§ 371 (c)(1),
(2) Date: Jan. 10, 2022

(87) PCT Pub. No.: WO2021/010878
PCT Pub. Date: Jan. 21, 2021

(65) Prior Publication Data
US 2022/0259129 A1    Aug. 18, 2022

(30) Foreign Application Priority Data
Jul. 18, 2019    (SE) .................................... 1930249-6

(51) Int. Cl.
*B01D 1/06*    (2006.01)
*B01J 31/18*    (2006.01)
(Continued)

(52) U.S. Cl.
CPC .............. *C07C 45/82* (2013.01); *B01D 1/065* (2013.01); *B01J 31/185* (2013.01); *C07C 45/50* (2013.01)

(58) Field of Classification Search
CPC ......... C07C 45/50; C07C 45/82; B01D 1/065; B01J 31/185
See application file for complete search history.

(56) References Cited

U.S. PATENT DOCUMENTS 4,151,209 A * 4/1979 Paul ........................ C07C 45/50
568/454
4,297,239 A 10/1981 Bryant et al.
(Continued)

FOREIGN PATENT DOCUMENTS

EP    0404193 A1    12/1990
EP    0423769 A2    4/1991
(Continued)

OTHER PUBLICATIONS

International Search Report and Written Opinion dated Jul. 13, 2020 for corresponding PCT Application No. PCT/SE2020/050612.

*Primary Examiner* — Jonathan Miller
(74) *Attorney, Agent, or Firm* — POLSINELLI PC

(57) ABSTRACT

Use of a method for reduction of heavy end formation and catalyst loss in a hydroformylation process, wherein the method comprises the steps;
a) Reacting an olefin and syngas in a reactor assembly (1) utilizing at least one catalyst and at least one ligand,
b) Separating an obtained aldehyde from a mixture of aldehyde, catalyst, ligand and early heavy ends in a distillation unit (2),
c) Entering the mixture of catalyst, ligand, early heavy ends and rest aldehyde into a short residence time evaporator unit (3) having at least a first rest aldehyde stripper stage
(Continued)

(3a) and at least one last early heavy ends stripper stage (3b). Said evaporator units (3) being of a falling film and/or wiped film type, d) That the catalyst/ligand mixture from a lower end (3b1) of the at least one last early heavy ends stripping stage (3b) is entered into a cooling unit (4) immediately after stripping of early heavy ends.

17 Claims, 1 Drawing Sheet

(51) Int. Cl.
*C07C 45/50* (2006.01)
*C07C 45/82* (2006.01)

(56) References Cited

U.S. PATENT DOCUMENTS

| | | | | |
|---|---|---|---|---|
| 4,760,194 A * | 7/1988 | Phillips | ............ | C07C 45/49 502/166 |
| 5,364,950 A * | 11/1994 | Babin | ............ | C07C 45/50 568/429 |
| 5,672,766 A * | 9/1997 | Mori | ............ | C07C 45/50 568/454 |
| 5,763,671 A * | 6/1998 | Bryant | ............ | C07F 9/025 568/454 |
| 6,153,800 A * | 11/2000 | Gelling | ............ | C07F 9/145 568/454 |
| 6,610,891 B1 * | 8/2003 | O'Young | ............ | B01J 31/185 568/454 |
| 8,907,129 B2 * | 12/2014 | Grass | ............ | C07C 45/50 562/512.2 |
| 2004/0054236 A1 * | 3/2004 | Ueda | ............ | C07C 45/50 568/451 |
| 2007/0282132 A1 * | 12/2007 | Beadle | ............ | C07C 45/50 568/451 |
| 2019/0047930 A1 | 2/2019 | Becker et al. | | |

FOREIGN PATENT DOCUMENTS

| | | |
|---|---|---|
| GB | 2192182 A | 1/1988 |
| JP | H08165266 A | 6/1996 |
| RU | 2561171 C1 | 8/2015 |
| WO | 2017083106 A1 | 5/2017 |

* cited by examiner

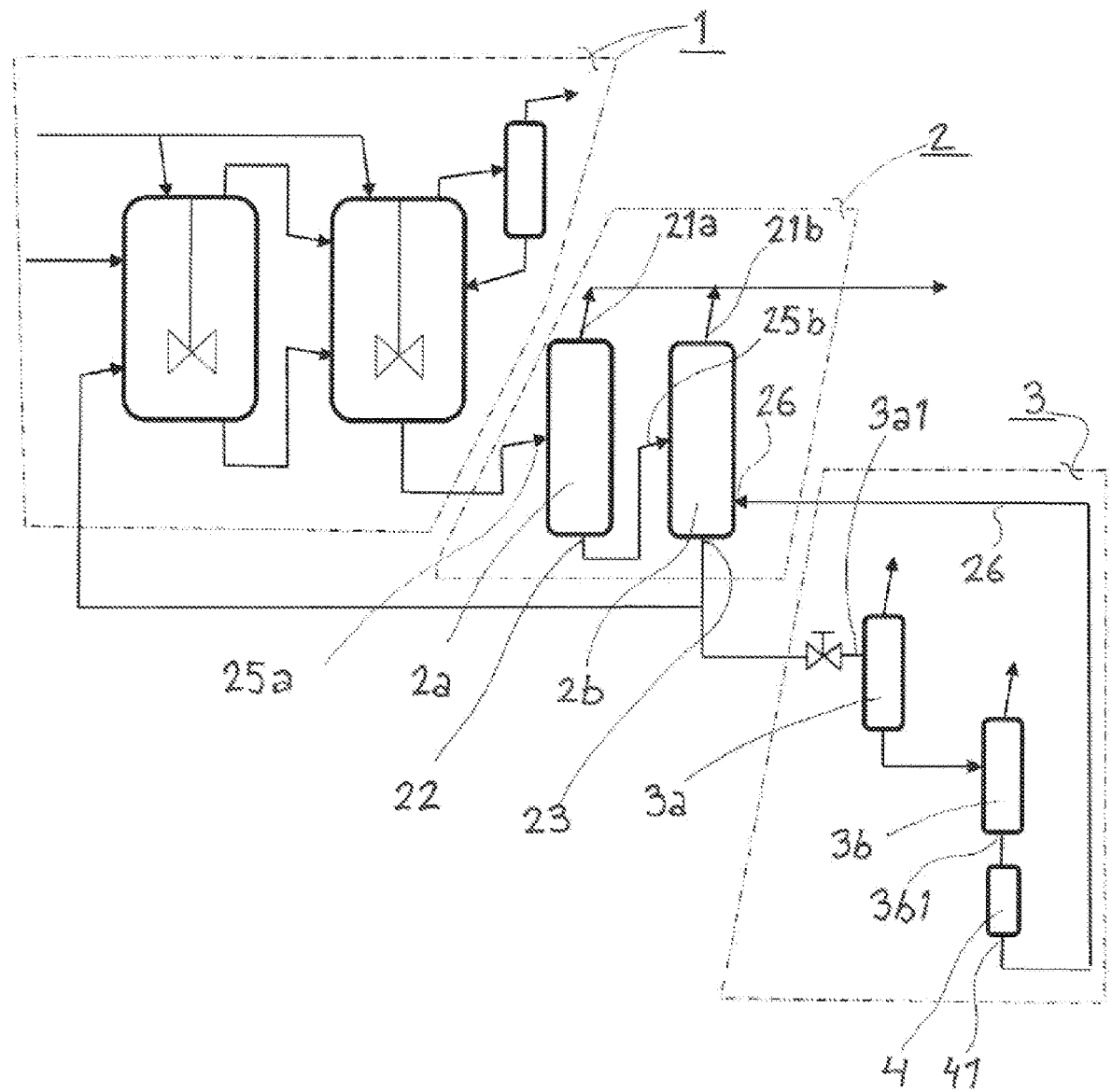

USE OF A METHOD FOR REDUCTION OF HEAVY END FORMATION AND CATALYST LOSS IN A HYDROFORMYLATION PROCESS COMPRISING A BIDENTATE PHOSPHITE LIGAND

CROSS-REFERENCE TO RELATED APPLICATIONS

This application is a national stage application (under 35 U.S.C. § 371) of PCT/SE2020/050612, filed Jun. 12, 2020, which claims benefit of Swedish Application No. 1930249-6, filed Jul. 18, 2019, which are incorporated herein by reference in their entireties.

The present invention refers to the use of a method for reducing the presence of heavy ends in a continuous hydroformylation process, where an olefin or an olefin mixture is reacted with carbon monoxide and hydrogen in the presence of a rhodium complex catalyst, comprising at least one organobisphosphite ligand, in order to produce an aldehyde. Said use comprising the continuous or discontinuous removal of early heavy ends.

Hydroformylation, also called the oxo process, is an important industrial process that generates aldehydes by reacting olefins with carbon monoxide and hydrogen in the presence of transition metal catalyst complexes. It is well known that preferred processes involve continuous hydroformylation and recycling of a catalyst solution containing a metal-organophosphorus ligand complex catalyst wherein the metal is a Group VIII transition metal, preferably rhodium. Such art is exemplified by for instance U.S. Pat. Nos. 4,148,830, 4,717,775, and 4,769,498. Yielded aldehydes have a wide range of utility, for example, as intermediates for hydrogenation to aliphatic alcohols, so called oxo alcohols, for amination to aliphatic amines, for oxidation to aliphatic acids, and for aldol condensation to produce components of plasticizers.

Rhodium catalysts need ligands for stabilizing and/or activating the rhodium in rhodium-catalyzed low-pressure hydroformylation. Rhodium complexed with phosphorus ligands, wherein the phosphorus ligands typically are organophosphines and/or organophosphites, are well known in the art. Rhodium-bisphosphite catalysts are known to be used in the hydroformylation of linear olefins, like propenes, butenes and hexenes and they have an effect of increased activity and selectivity to unbranched reaction products.

Hydroformylation is often accompanied by a series of parallel and secondary reactions. Due to their high reactivity the formed aldehydes undergo aldol condensation reactions, Tischenko reactions and acetalization reactions and produce high-boiling by-products, such as dimers, trimers and tetramers. These high-boiling by-products produced during the hydroformylation process are called heavy ends and they can cause a lot of problems to the process, since their accumulation can lead to a forced bleeding of rhodium and ligand containing solution. Heavy ends formation can take place in reactors, as well as in hot places like lower end of evaporators.

Referring to the accompanying FIGURE, the present invention relates to the use of a method for reduction of heavy end formation and catalyst loss in a hydroformylation process, wherein the method comprises the steps;
a) reacting an olefin and syngas in a reactor assembly (1) utilizing at least one catalyst and at least one ligand,
b) separating an obtained aldehyde from a mixture of aldehyde, catalyst, ligand and early heavy ends in a distillation unit (2),
c) entering the mixture of catalyst, ligand, early heavy ends and rest aldehyde into a short residence time evaporator unit (3) having at least a first rest aldehyde stripper stage (3a) and at least one last early heavy ends stripper stage (3b). Said evaporator units (3) being of a falling film and/or wiped film type,
d) that the catalyst/ligand mixture from a lower end (3b1) of the at least one last early heavy ends stripping stage (3b) is entered into a cooling unit (4) immediately after stripping of early heavy ends.

The term "early heavy ends" are to be understood as high boiling reaction products unintentionally obtained through for example aldol condensation, Tischenko reaction, acetalization and oxidation as the aldehydes produced are highly reactive. Early heavy ends will over time gradually become more complex heavy ends with even higher boiling point. The term "early heavy ends" are therefore to be understood as heavy ends that are possible to separate in an evaporator under conditions mild enough not to cause thermal degradation of the organophosphite ligand utilized. In embodiment examples of this invention temperatures at or below about 170° C. and vacuum at or below 3 mbar have been utilized.

Use of the process of the present invention is advantageously and preferably used in a hydroformylation of at least one $C_2$-$C_6$ olefin, such as ethylene, a propene, a butene, including 1-butene and cis- or trans-2-butene, a pentene and/or a hexene, in presence of at least one Group VIII transition metal, such as ruthenium, palladium, osmium, iridium, platinum and rhodium, catalyst or catalyst precursor.

The at least one last early heavy ends stripping stage (3b) suitably have a short path and is operated in the range 0.1-3 mbar and at a temperature in the range 130-170° C.

According to one embodiment of the invention the distillation unit (2) have at least a first and a final stage (2a and 2b respectively) where all stages (2a and 2b respectively) have an upper outlet (21a and 21b respectively) for aldehyde, a central inlet (25a and 25b respectively) for the mixture of aldehyde, catalyst, ligand and early heavy ends and lower outlets (22 and 23 respectively) for the mixture of rest aldehyde, catalyst, ligand and early heavy ends. The final stage (2b) is premeditated to feed the mixture of rest aldehyde, catalyst, ligand and early heavy ends to a heavy end separator inlet (3a1) from the final stage (2b) lower outlet (23).

The cooling unit (4) have an outlet (41) through which the recovered, through the process purified, catalyst/ligand mixture is fed back to the reactor assembly (1).

The mixture of rest aldehyde, catalyst, ligand and early heavy ends stream from the final stage (2b) lower outlet (23) is fed in part back to the reactor assembly and in part through the heavy end separator inlet (3a1) into the evaporator unit (3).

This set up will allow a smaller and more cost effective early heavy end separation evaporator unit. Smaller evaporator units will also allow for shorter residence time and short path which is a highly desired property in order not to cause thermal breakdown of the ligands. It has shown through calculations and process simulation that allowing as little as below 10% or even 1% of the catalyst/ligand return flow to the reactor to pass through a heavy end stripping stage is sufficient to separate early heavy ends from the process.

According to one embodiment of the invention the recovered catalyst and ligand mixture from the outlet (41) of the cooling unit (4) is fed back to the reactor assembly (1) via a return inlet (26) of the final stage (2b) of the distillation unit (2).

The catalyst is a transition metal selected from the group consisting of; cobalt and rhodium while the ligand is a phosphite ligand, preferably an organobisphosphite ligand.

In a most preferred embodiment of the invention the ligand is a organobisphosphate ligand of formula I;

Formula (I)

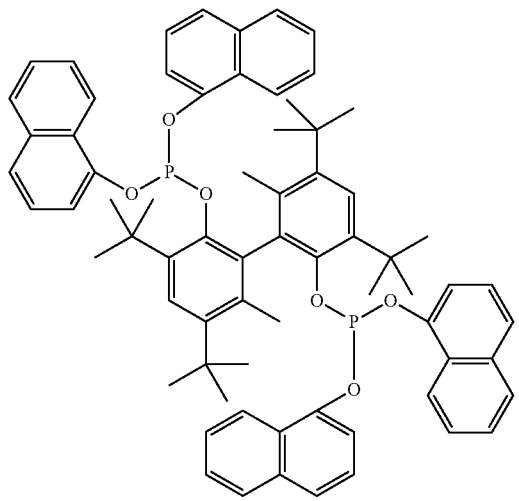

and the catalyst mixture is a rhodium organophosphite ligand complex.

The separation of early heavy ends is in accordance with one embodiment of the invention performed discontinuously at regular intervals through means of analysis of heavy end presence in the catalyst/ligand mixture stream. The analysis can be performed either manually or through automation.

The separation of early heavy ends can in accordance with another embodiment of the invention be performed continuously. The continuous separation of early heavy ends can accordingly be guided through means of statistical process guiding, where analysis of heavy end presence in the catalyst/ligand mixture stream is the regulating the flow, i.e. kg/hour, through the evaporator unit (3) as well as at least the temperature in the early heavy ends stripper stage (3b).

The olefin is suitably a C2-C6 olefin.

In accordance with a preferred embodiment of the invention the olefin is 1-butene and possibly cis- and/or trans-2-butene.

Experimental—Heavy End Analysis

Catalyst/ligand mixture i.e. a rhodium/bisphosphite ligand A4N3 (CAS 198979-98-5) which had been in use in hydroformylation process for aldehyde production for longer than 6 months was analyzed in respect of heavy end content. Accordingly, the heavy end content did have ample time to build up through aldol condensation, Tischenko reaction, acetalization and oxidation as aldehydes produced in the hydroformylation process are highly reactive. The results from the analysis is presented in table 1.

TABLE 1

| Heavy end [type] | Presence [wt %] |
| --- | --- |
| C5 | 5% |
| C10 | 5% |

TABLE 1-continued

| Heavy end [type] | Presence [wt %] |
| --- | --- |
| C15 | 25% |
| C20 | 16% |
| >C20 | 33% |
| >>C20 *) | 16% |

*) Heavy ends much heavier than C20 are difficult to analyze due to their complexity.

Experimental—Heavy End Separation.

Experiments were carried out in a laboratory set up, simulating continuous hydroformylation of 1-butene and syngas utilizing the catalyst/ligand mixture defined above. The aldehydes were distilled off in an evaporator and the heavy ends were separated from the remaining catalyst/ligand and heavy end mixture in a falling film evaporator with short residence time and short path. The pressures, temperature, amount of heavy ends separated is presented in table 2.

TABLE 2

| Temperature [° C.] | Pressure [mbar] | C10 [wt %] | C15 [wt %] | C20 [wt %] | >C20 [wt %] | >>C20*) [wt %] |
| --- | --- | --- | --- | --- | --- | --- |
| 170 | 0.5 | 93 | 42 | 29 | 15 | 1 |
| 170 | 3.0 | 79 | 32 | 19 | 12 | 0 |
| 170 | 3.0 | 89 | 33 | 18 | 11 | 0 |

*)Heavy ends much heavier than C20 are difficult to analyze due to their complexity.

Observations and Conclusions;

It shows that the lighter heavy ends are easily separated from the catalyst/ligand mixture to a very high degree under these relatively mild conditions. We also observed that lighter ligand degradation products were separated from the catalyst/ligand mixture. Such ligand degradation products are known to contribute as catalyst in degradation of intact ligands. The herein described invention will accordingly prevent not only loss of costly rhodium catalyst through bleeding out together with complex heavy ends, it will also increase the life span of the delicate organophosphite ligand. Due to radical reduction of complex heavy ends, interruptions in production will also be less occurring. The radical reduction of complex heavy ends is achieved by continuous or recurrent separation of the early heavy ends from the reaction/product solution stream as it takes from days, weeks or even months for the complex, >C20→>>C20, heavy ends to form, all depending on production parameters.

The invention claimed is:
1. A method for reducing heavy end formation and catalyst loss in a hydroformylation process comprising:
   (a) reacting an olefin and syngas in a reactor assembly (1) utilizing at least one catalyst and at least one ligand;
   (b) separating an obtained aldehyde from a mixture of aldehyde, catalyst, ligand, and early heavy ends in a distillation unit (2);
   (c) directing part of a mixture of catalyst, ligand, early heavy ends, and residual aldehyde into a short residence time evaporator unit (3) having at least a first residual aldehyde stripper stage (3a) and at least one last early heavy ends stripper stage (3b), the evaporator unit (3) being a falling film and/or wiped film type; and
   (d) directing a catalyst/ligand mixture from a lower end (3b1) from the at least one last early heavy ends stripping stage (3b) into a cooling unit (4) immediately after stripping of early heavy ends, wherein the distillation unit (2) comprises:
  at least a first and a final stage (2a and 2b respectively) where all stages (2a and 2b respectively) comprises:
    upper outlets (21a and 21b respectively) for aldehyde;
    central inlets (25a and 25b respectively) for the mixture of aldehyde, catalyst, ligand, and early heavy ends; and
    lower outlets (22 and 23 respectively) for the mixture of residual aldehyde, catalyst, ligand, and early heavy ends;
      wherein the final stage (2b) directs the mixture of residual aldehyde, catalyst, ligand, and early heavy ends to a heavy end separator inlet (3a1) from the final stage (2b) lower outlet (23), and
      the mixture of residual aldehyde, catalyst, ligand, and early heavy ends from the final stage (2b) lower outlet (23) is returned, at least in part, to the reactor assembly and through the heavy end separator inlet (3a1) into the evaporator unit (3).

2. The method of claim 1, wherein the at least one last early heavy ends stripping stage (3b) comprises a short path and is operated in the range 0.1 to 3 mbar at a temperature in the range of 130 to 170° C.

3. The method of claim 1, wherein the cooling unit (4) comprises an outlet (41) through which a recovered catalyst/ligand mixture is returned to the reactor assembly (1).

4. The method of claim 3, wherein the recovered catalyst/ligand mixture is returned to the reactor assembly (1) via a return inlet (26) of the final stage (2b) of the distillation unit (2).

5. The method of claim 1, wherein the catalyst is a transition metal chosen from cobalt, rhodium, and a mixture thereof.

6. The method of claim 1, wherein the ligand is a phosphite ligand.

7. The method of claim 6, wherein the ligand is a organobisphosphite ligand.

8. The method of claim 7, wherein the ligand is a organobisphosphate ligand of formula I:

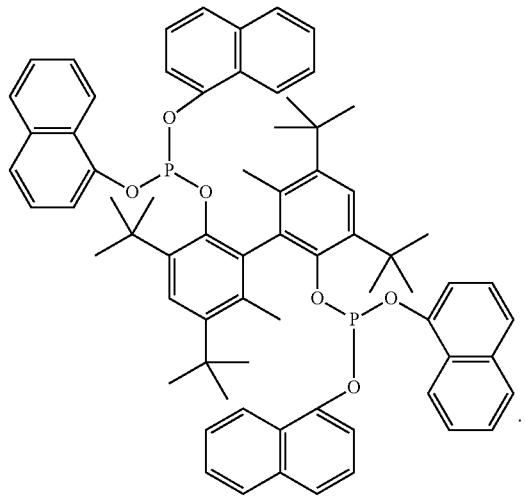

Formula (I)

9. The method of claim 5, wherein the catalyst mixture is a rhodium organophosphite ligand complex.

10. The method of claim 1, wherein the separation of early heavy ends is performed discontinuously at regular intervals by analysis of heavy end presence in the catalyst/ligand mixture.

11. The method of claim 1, wherein the separation of early heavy ends is performed continuously.

12. The method of claim 11, wherein the continuous separation of early heavy ends is guided by statistical process guiding, wherein analysis of heavy end presence in the catalyst/ligand mixture regulates flow through the evaporator unit (3) and regulates at least the temperature in the early heavy ends stripper stage (3b).

13. The method of claim 1, wherein the olefin is a $C_2$-$C_6$ olefin.

14. The method of claim 1, wherein the olefin is 1-butene.

15. The method of claim 1, wherein the olefin further comprises cis- and/or trans-2-butene.

16. The method of claim 5, wherein the olefin is a $C_2$-$C_6$ olefin.

17. The method of claim 5, wherein the olefin is 1-butene.

* * * * *